US00PP34236P2

(12) United States Plant Patent
Bradford et al.

(10) Patent No.: US PP34,236 P2
(45) Date of Patent: May 17, 2022

(54) NECTARINE TREE NAMED 'PEARLICIOUS XXIV'

(50) Latin Name: *Prunus persica*
Varietal Denomination: Pearlicious XXIV

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,920

(22) Filed: Dec. 17, 2021

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

PP18,751 P2 4/2008 Bradford
PP30,145 P2 1/2019 Bradford

*Primary Examiner* — Susan McCormick Ewoldt

(57) ABSTRACT

The present invention relates to a new and distinct variety of nectarine tree, *Prunus persica*, broadly characterized by a small to medium size, moderately vigorous, hardy, self-fertile, productive and regular bearing tree. The variety blooms during the late season and requires about 650 chilling hours. The fruit matures under the ecological conditions described in early October, with first picking on Oct. 1, 2021. The fruit is medium to large in size, a balance of high sugar with slight acid in flavor, fairly globose in shape, clingstone in type, firm in texture, white in flesh color, mostly red in skin color, and has a bitter tasting kernel.

1 Drawing Sheet

Botanical classification: *Prunus persica.*
Variety denomination: 'PEARLICIOUS XXIV'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious XXIV'.

In 2011 we made a first generation hybridization using '37P398' (unpatented) nectarine as the selected seed parent and 'Autumn Bright' (U.S. Plant Pat. No. 18,751) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2015 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '37P398' (unpatented) nectarine, by being self-fertile and by producing nectarines that are white in flesh color, that are clingstone in type, that are medium to large in size, and that are low in acid, but is distinguished from it by having a small instead of large blossom and by producing fruit that is darker red in skin color, that is substantially sweeter in flavor, that is firmer in texture and that matures about ten days later.

The present variety is similar to its pollen parent, 'Autumn Bright' (U.S. Plant Pat. No. 18,751) nectarine, by being self-fertile, by requiring about 650 chilling hours, and by producing nectarines that are mostly red in skin color, clingstone in type, and firm in texture, but is quite distinguished from it by producing fruit that is somewhat larger in size, that is white instead of yellow in flesh color, and that ripens about twenty days later.

The present variety is most similar to 'Pearlicious XX' (U.S. Plant Pat. No. 30,145) nectarine by being self-fertile, by requiring about 650 chilling hours, by blooming in the late season, by having reniform leaf glands, by having a bitter kernel, and by producing nectarines that are white in flesh color, that are clingstone in type, that are firm in texture, and that are sweet in flavor, but is distinguished therefrom by having a small instead of large blossom, and by producing nectarines that are larger in size, that are much darker red in skin color, and that mature about 5 days later.

SUMMARY OF VARIETY

In summary, the present nectarine variety is characterized by a small to medium size, moderately vigorous, hardy, self-fertile, productive and regular bearing tree. The variety blooms during the late season and requires about 650 chilling hours. The fruit matures under the ecological conditions described in early October, with first picking on Oct. 1, 2021. The fruit is medium to large in size, a balance of high sugar with slight acid in flavor, fairly globose in shape, clingstone in type, firm in texture, white in flesh color, mostly red in skin color, and has a bitter tasting kernel.

DRAWING

The accompanying photograph consists of four whole fruits positioned to display the characteristics of the skin color and form, one divided fruit to reveal the flesh and stone, typical leaves, and two insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Oct. 4, 2021, on the original tree during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: '37P398' (unpatented) nectarine.

Pollen parent: 'Autumn Bright' (U.S. Plant Pat. No. 18,751) nectarine.

TREE

Size: Small to medium, reaching and maintaining a height of 10' [3.05 m.] and a spread of 7' [2.13 m.] after ten growing seasons utilizing typical dormant pruning.

Vigor: Moderately vigorous, responding about average to irrigation and fertilization. The variety grows about 2' [0.61 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 650 hours.

Leaf bud burst: Medium to late, during the end of flowering.

Trunk:

- *Size*.—Slender, reaching a maximum diameter of 4¾" [120.7 mm.] after the tenth growing season.
- *Texture*.—Rough to shaggy.
- *Bark color*.—A Light grayish brown [60. l.gy.Br] and Grayish brown [61. gy.Br] variegation with Dark grayish brown [62. d.gy.Br] crevices present.
- *Lenticels*.—Approximate Number Per Square Inch: 10. Color: Deep orange yellow [69. deep OY]. Average Size: ⅜" [9.5 mm.] in length. The width is typically one fourth as much as the length. Shape: Elongated.

Branches:

- *Size*.—Medium to slender, diameter of main scaffold is 2¾" [69.9 mm.] measured 12" above the first hanger, diameter of lowest hanger is 1¼" [31.8 mm.].
- *Texture*.—Smooth to medium on first and second year wood, increasing in roughness with age.
- *Color*.—1st Year Wood Topside: Grayish red [19. gy.R]. 1st Year Wood Underside:. Brilliant yellow green [116. brill.YG]. Older Wood: A Grayish yellowish brown [80. gy.yBr] and Moderate yellowish brown [77. m.yBr] variegation with Deep yellowish brown [75. deep yBr] crevices present.
- *Lenticels*.—Number Per Square Inch: About 25 on second year wood. Color: Strong yellowish brown [74. s.yBr]. Average Size: Medium, 1/16" [1.6 mm.] in length. The width is typically one fourth as much as the length. Shape: Elongated.

Leaves:

- *Size*.—Large. Average Length: 6½" [165.1 mm.]. Average Width: 1 11/16" [42.9 mm.].
- *Arrangement*.—Alternate.
- *Thickness*.—Medium.
- *Form*.—Elliptical.
- *Apex*.—Acuminate.
- *Base*.—Acute, with an average base angle of 70 degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: ½" [12.7 mm.]. Average Thickness: 1/16" [1.6 mm.]. Color: Light yellow green [119. l.YG].
- *Stipules*.—Number: 2 per leaf, up to 6 per growing tip. Average Length: ¼" [6.4 mm.]. Color: Vivid yellow green [115. v.YG] becoming Moderate brown [58. m.Br] with age.
- *Glands*.—Number: 2 to 4 per leaf. Position: Mostly opposite with a few alternate, first pair is located at the intersection of petiole and base of blade. Form: Reniform. Size: Medium, about 1/32" [0.8 mm.] in length. Color: Light yellow green [119. l.YG] becoming Dark olive brown [96. d.OlBr] with age.
- *Leaf buds*.—Pointed.

Flower buds:

- *Hardiness*.—Hardy, with respect to central California blooming season.
- *Diameter*.—Typically ⅜" [9.5 mm.] 1 week before bloom.
- *Length*.—Typically ⅝" [15.9 mm.] 1 week before bloom.
- *Form*.—Not appressed.
- *Surface*.—Pubescent.
- *Tip color*.—Moderate purplish pink [250. m.pPk] with the stigma occasionally protruding.

Flowers: Perfect, complete, perigynous, usually a single pistil, about thirty stamens, five sepal and petal locations alternately positioned.

*Type*.—Non-showy, small.
*Average flower diameter*.—1 5/16" [33.3 mm.].
*Average flower depth*.—5/16" [7.9 mm.] when fully open.
*Average pedicel length*.—1/8" [3.2 mm.].
*Number of petals*.—Mostly five, extra petal fragments occasional, double blossoms not observed.
*Petal arrangement*.—Non-overlapping.
*Petal shape*.—Obovate.
*Petal margin*.—Entire, somewhat wavy.
*Average petal diameter*.—7/16" [11.1 mm.].
*Average petal length*.—9/16" [14.3 mm.].
*Petal apex*.—Rounded.
*Petal base*.—Slightly acute.
*Petal color*.—Deep purplish pink [248. deep pPk] toward the apex, Light purplish pink [249. l.pPk] in the center and toward the base on both sides.
*Anther color*.—Moderate reddish orange [37. m.rO] surrounding a Light yellow [86. l.Y] center at bloom onset.
*Pollen*.—Anthers produce an abundance of Brilliant yellow [83. brill.Y] pollen.
*Stigma color*.—Light greenish yellow [101. l.gY].
*Stigma position*.—Typically located about 1/8" [3.2 mm.] above nearby anthers.
*Stamen position*.—Typically located about 1/16" [1.6 mm.] below the petals.
*Average pistil length*.—3/4" [19.1 mm.].
*Average stamen length*.—1/2" [12.7 mm.].
*Ovary*.—Non-pubescent.
*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—5/16" [7.9 mm.].
*Sepal width*.—1/4" [6.4 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Late compared to other varieties, blooms at the same time as 'Autumn Bright' (U.S. Plant Pat. No. 18,751) nectarine.
*Onset of bloom*.—One percent on Feb. 26, 2021.
*Date of full bloom*.—Mar. 8, 2021.
*Duration of bloom*.—One to two weeks, dependent on ambient temperature.
*Bloom density*.—Heavy.
*Number per cluster*.—1 to 3 with single flowers most common.

FRUIT

Maturity when described: Shipping ripe, Oct. 4, 2021.
Date of first picking: Oct. 1, 2021.
Date of last picking: Oct. 15, 2021.
Size: Uniform, medium to large.
*Average diameter axially*.—3" [76.2 mm.].
*Average diameter across suture plane*.—3 1/16" [77.8 mm.].
*Average diameter across cheek plane*.—3" [76.2 mm.].
*Typical weight*.—9.1 ounces [258 grams].
Form: Variable, mostly globose, a few asymmetrical.
*Longitudinal section form*.—Round to round ovate.
*Axial view*.—Round to slightly oval.
Suture: Extends from the base, along the side, and ending about 1/2" [12.7 mm.] beyond the pistil point.
*Near the base*.—A shallow groove.
*Along the side*.—A very shallow trough.
*Near the apex*.—A shallow groove.
Ventral surface: Rounded, lipped stronger toward the apex.
Lips: Unequal toward the apex on most.
Cavity: Flaring, circular, suture showing on one side, Pale yellow [89. p.Y] stem markings present.
*Depth*.—5/8" [15.9 mm.].
*Breadth*.—1 1/4" [31.8 mm.].
Base: Truncate, slightly cordate if viewed parallel to the suture.
Apex: Rounded, cordate if viewed parallel to the suture.
Pistil point: Apical, 1/16" [1.6 mm.] in length, mostly depressed within the suture.
Stem: Medium.
*Average length*.—3/8" [9.5 mm.].
*Average width*.—3/16" [4.8 mm.].
Skin:
*Thickness*.—Medium.
*Surface*.—Smooth.
*Tenacity*.—Tenacious to the flesh.
*Astringency*.—Slightly astringent.
*Tendency to crack*.—Slight.
*Color*.—Very dark red [14. v.deep R] over a Moderate red [15. m.R] background with some Pale greenish yellow [104. p.gY] areas where sun protected and moderate Pale yellow [89. p.Y] freckling toward the apex.
Flesh:
*Color*.—White [263. White] with Vivid dark red [17. v.d.R] streaking next toward the stone.
*Surface of pit cavity*.—Covered with Vivid dark red [17. v.d.R] broken fibers when twisted away from the stone.
*Amygdalin*.—Scarce.
*Juice*.—Abundant, rich.
*Texture*.—Firm, crisp.
*Fibers*.—Few, tender.
*Ripens*.—Fairly evenly.
*Flavor*.—A tasty balance of high sugar with slight acid, typically 20 brix.
*Aroma*.—Very slight.
*Eating quality*.—Very good.

STONE

Type: Clingstone.
Form: Oval.
Hilum: Narrow, oval.
Base: Truncate.
Apex: Acute to rounded.
Sides: Equal.
Tip: Sharp, 1/8" [3.2 mm.] in length.
Surface: Irregularly furrowed toward the apex, pitted toward the base.
Ridges: Jagged.
External color: Vivid dark red [17. v.d.R] when first removed.
Pit wall color when cracked: Strong brown [55. s.Br].
Cavity surface color: Strong brown [55. s.Br] with Dark brown [59. d.Br] marbling.

Average pit wall thickness: ¼" [6.4 mm.].
Average length: 1 9/16" [39.7 mm.].
Average width: 1⅛" [28.6 mm.].
Average breadth: 13/16" [20.6 mm.].
Tendency to split: None observed.
Kernel:

*Form*.—Oval.
*Skin color*.—Brownish orange [54. brO].
*Pellicle color*.—Dark brown [59. d.Br].
*Vein color*.—Strong brown [55. s.Br].
*Taste*.—Bitter.
*Viable*.—Yes.
*Average length*.—¾" [19.1 mm.].
*Average width*.—9/16" [14.3 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious XX' (U.S. Plant Pat. No. 30,145) nectarine by being self-fertile, by requiring about 650 chilling hours, by blooming in the late season, by having reniform leaf glands, by having a bitter kernel, and by producing nectarines that are white in flesh color, that are clingstone in type, that are firm in texture, and that are sweet in flavor, but is distinguished therefrom by having a small instead of large blossom, and by producing nectarines that are larger in size, that are much darker red in skin color, and that mature about 5 days later.

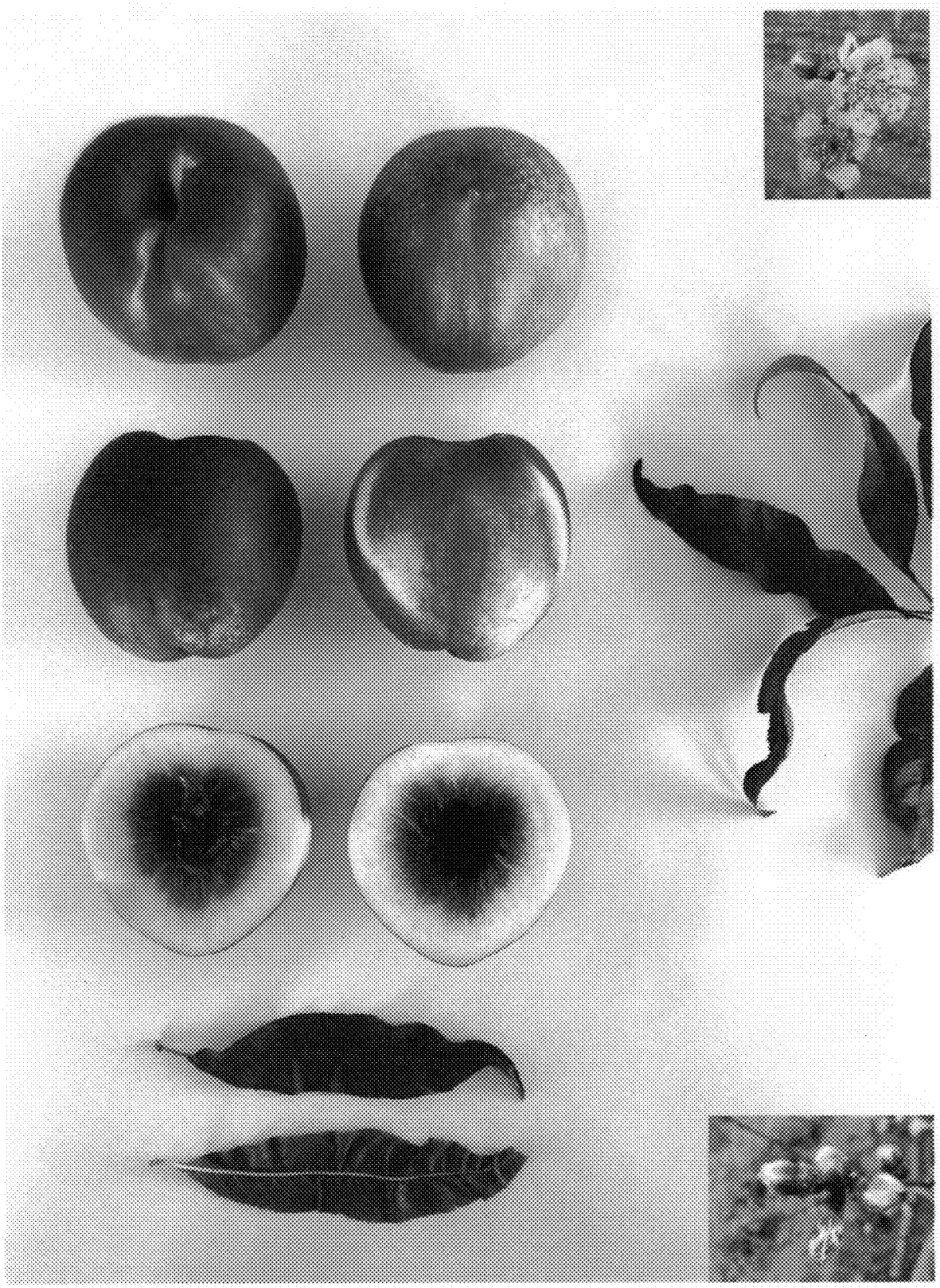

* * * * *